US011592441B2

(12) United States Patent
Lee et al.

(10) Patent No.: US 11,592,441 B2
(45) Date of Patent: Feb. 28, 2023

(54) NANOPLASMONIC SENSOR AND KIT FOR BIOMOLECULE ANALYSIS, AND METHOD OF ANALYZING BIOMOLECULE USING THE SAME

(71) Applicants: KOREA RESEARCH INSTITUTE OF STANDARDS AND SCIENCE, Daejeon (KR); FOUNDATION FOR RESEARCH AND BUSINESS, SEOUL NATIONAL UNIVERSITY OF SCIENCE AND TECHNOLOGY, Seoul (KR)

(72) Inventors: Tae Geol Lee, Daejeon (KR); Hee Kyung Na, Daejeon (KR); Jung Sub Wi, Daejeon (KR); Jong G. OK, Seoul (KR)

(73) Assignees: KOREA RESEARCH INSTITUTE OF STANDARDS AND SCIENCE, Daejeon (KR); FOUNDATION FOR RESEARCH AND BUSINESS, SEOUL NATIONAL UNIVERSITY OF SCIENCE AND TECHNOLOGY, Seoul (KR)

( * ) Notice: Subject to any disclaimer, the term of this patent is extended or adjusted under 35 U.S.C. 154(b) by 613 days.

(21) Appl. No.: 16/216,306

(22) Filed: Dec. 11, 2018

(65) Prior Publication Data

US 2020/0072830 A1 Mar. 5, 2020

(30) Foreign Application Priority Data

Sep. 3, 2018 (KR) .................. KR10-2018-0104767

(51) Int. Cl.
*G01N 33/543* (2006.01)
*G01N 21/552* (2014.01)
*G01N 21/77* (2006.01)

(52) U.S. Cl.
CPC ..... *G01N 33/54373* (2013.01); *G01N 21/554* (2013.01)

(58) Field of Classification Search
None
See application file for complete search history.

(56) References Cited

U.S. PATENT DOCUMENTS 6,761,816 B1 * 7/2004 Blackburn ........... C12Q 1/6825
205/777.5
7,405,054 B1 * 7/2008 Hasenbank ...... G01N 33/54373
435/7.9

(Continued)

FOREIGN PATENT DOCUMENTS

JP 2002501174 1/2002
JP 2002253232 9/2002

(Continued)

OTHER PUBLICATIONS

Varallyay et al, Nature Protocols, vol. 3, pp. 190-196, published online Jan. 17, 2008.*

(Continued)

*Primary Examiner* — Robert T. Crow
(74) *Attorney, Agent, or Firm* — Cantor Colburn LLP

(57) ABSTRACT

Provided is a nanoplasmonic sensor and a kit for biomolecule analysis, and a method of analyzing a biomolecule using the same. The method includes: providing the nanoplasmonic sensor including a dielectric grating extending in one direction, and a metal structure disposed to cover an upper surface and a side surface of the dielectric grating and have at least one bent portion; immobilizing a first probe molecule on a surface of the metal structure; hybridizing an analyte with the first probe molecule by introducing the analyte having a base sequence complementary to the first probe molecule; binding a second probe molecule that is hybridized with the first probe molecule to the analyte;

(Continued)

binding an enzyme to the second probe molecule; introducing a substrate that reacts with the enzyme to produce a precipitate by an enzymatic reaction; and measuring localized surface plasmon resonance in the metal structure.

12 Claims, 9 Drawing Sheets

Specification includes a Sequence Listing.

(56) References Cited

U.S. PATENT DOCUMENTS

| | | | |
|---|---|---|---|
| 2002/0123155 A1 | 9/2002 | Himmelhaus et al. | |
| 2005/0064432 A1 | 3/2005 | Huang et al. | |
| 2006/0014144 A1 | 1/2006 | Christensen et al. | |
| 2006/0119853 A1* | 6/2006 | Baumberg | G01N 21/658 356/445 |
| 2007/0111382 A1* | 5/2007 | Huang | H01L 24/12 257/E23.021 |
| 2008/0144027 A1* | 6/2008 | Homola | G01N 21/553 356/317 |
| 2011/0166045 A1 | 7/2011 | Dhawan et al. | |
| 2012/0077191 A1* | 3/2012 | Gunning | C12Q 1/6834 435/6.11 |
| 2017/0052114 A1* | 2/2017 | Lin | G01N 21/554 |

FOREIGN PATENT DOCUMENTS

| | | |
|---|---|---|
| KR | 20090054096 | 5/2009 |
| WO | 1999035499 | 7/1999 |

OTHER PUBLICATIONS

Na, et al., Discrimination of single nucleotide mismatches using a scalable, flexible, and transparent three-dimensional nanostructure-based plasmonic miRNA sensor with high sensitivity, Biosensors and Bioelectronics, 2018, pp. 39-45.

Japanese Office Action—Japanese Application No. 2018-221108 dated Jan. 7, 2020, citing Zhuang, et al., Sun, et al., JP 2002-501174, US 2011/0166045, US 2005/0064432, JP 2002-253232, and US 2006/0014144.

Japanese Office Action—Japanese Application No. 2018-221108 dated Sep. 1, 2020, citing Zhuang, et al., Sun, et al., JP 2002-501174, US 2005/0064432, JP 2002-253232, and US 2006/0014144.

Sun, et al., Ultrasensitive detection of nucleic acids and proteins using quartz crystal microbalance and surface plasmon resonance sensors based on target-triggering multiple signal amplification strategy, Anaiytica Chimica Acta, May 2017, vol. 978, pp. 42-47.

Zhuang, et al., PlasmonicAuNP/g—C3N4 Nanohybrid-based Photoelectrochemical Sensing Platform for Ultrasensitive Monitoring of Polynucleotide Kinase Activity Accompanying DNAzyme-Catalyzed Precipitation Amplification, ACS Applied Materials & Interfaces, Apr. 2015, vol. 7, No. 15, pp. 8330-8338.

Ding et al., Surface plasmon resonance biosensor for highly sensitive detection of microRNA based on DNA super-sandwich assemblies and streptavidin signal amplification, Analytica Chimica Acta, 2015, vol. 874, pp. 59-65.

Korean Office Action—Korean Application No. 10-2019-0106704 dated Dec. 9, 2020, citing Ding et al., KR 10-2009-0054096, and miRCURY® LNA® miRNA Detection Probes Handbook.

MiRCURY® LNA® miRNA Detection Probes Handbook, Qiagen, Oct. 2017.

* cited by examiner

NANOPLASMONIC SENSOR AND KIT FOR BIOMOLECULE ANALYSIS, AND METHOD OF ANALYZING BIOMOLECULE USING THE SAME

BACKGROUND

1. Field

The present disclosure relates to a nanoplasmonic sensor and a kit for biomolecule analysis, and a method of analyzing a biomolecule using the same, and more particularly, to a nanoplasmonic sensor and a kit for biomolecule analysis, using a localized surface plasmon resonance phenomenon in a metal structure, a probe molecule that is specifically bound to an analyte, and an enzymatic reaction on a surface of the metal structure, and a method of analyzing a biomolecule using the same.

2. Description of Related Art

Plasmon resonance is a phenomenon caused by a behavior of free electrons in a metal, and is a phenomenon in which free electrons of a metal surface collectively oscillate due to resonance with an electromagnetic field of a specific energy of light, when light enters between the metal surface and a dielectric.

Surface plasmon resonance (SPR) refers to a phenomenon in which resonance occurs due to quantized oscillation of free electrons propagating along a surface of a metal thin film. Meanwhile, a metal structure having a size of several nanometers to several hundreds of nanometers, which is made of a metal rather than a metal thin film, may have an electric dipole or multipole characteristic by inducing collective oscillation of electrons in a conduction band due to light of a specific wavelength incident from an external source. As a result, in a manner different to the bulk state, light in a corresponding wavelength band may be highly scattered and absorbed to increase an electromagnetic field in a local region, known as localized surface plasmon resonance (LSPR). Particularly, devices such as real time chemical/biological sensors have been extensively studied by way of using an optical phenomenon by plasmon resonance in a nanosized metal structure made of a noble metal such as gold (Au) or silver (Ag).

The scattering and absorption in the localized surface plasmon resonance are sensitive to changes in material, dispositional location, size and shape of metal structures. In addition, since change in a refractive index of neighboring materials may be significantly influenced, these properties may be utilized in biosensors for detecting biomolecular and chemical components.

SUMMARY

One of the technical problems to be solved by the technical idea of the present disclosure is to provide a nanoplasmonic sensor and a kit for biomolecule analysis, using a localized surface plasmon resonance phenomenon in a metal structure, a probe molecule that is specifically bound to an analyte, and an enzymatic reaction on a surface of the metal structure, and a method of analyzing a biomolecule using the same.

According to an aspect of the present inventive concept, a method for analyzing a biomolecule using a nanoplasmonic sensor includes: providing the nanoplasmonic sensor including a dielectric grating extending in one direction, and a metal structure disposed to cover an upper surface and a side surface of the dielectric grating and have at least one bent portion; immobilizing a first probe molecule on a surface of the metal structure; hybridizing an analyte with the first probe molecule by introducing the analyte having a base sequence complementary to the first probe molecule; binding a second probe molecule that is hybridized with the first probe molecule to the analyte; binding an enzyme to the second probe molecule; introducing a substrate that reacts with the enzyme to produce a precipitate by an enzymatic reaction; and measuring localized surface plasmon resonance in the metal structure.

According to an aspect of the present inventive concept, a nanoplasmonic sensor for biomolecule analysis includes: a sensing portion including at least one dielectric grating disposed on a base layer to extend in one direction, and a metal structure disposed to cover an upper surface and a side surface of the dielectric grating and have at least one bent portion; a material supplying portion sequentially providing: a first probe molecule, an analyte having a base sequence complementary to the first probe molecule, a second probe molecule that is hybridized with the first probe molecule, an enzyme that is bound to the second probe molecule, and a substrate that reacts with the enzyme to form a precipitate, to the metal structure; and a measurement portion for measuring localized surface plasmon resonance phenomenon in the metal structure, including a light source unit disposed on an upper portion of the base layer and generating incident light incident on the metal structure, and a light receiving unit disposed on a lower portion of the base layer and detecting a change in optical characteristics in the metal structure.

According to an aspect of the present inventive concept, a kit for biomolecule analysis includes: at least one dielectric grating disposed on a base layer to extend in one direction; a metal structure disposed to cover an upper surface and a side surface of the dielectric grating and have at least one bent portion; a first probe molecule hybridized with an analyte and bound to a surface of the metal structure; a second probe molecule hybridized with the first probe molecule at an end not bound to the analyte; an enzyme bound to the second probe molecule; and a substrate reacting with the enzyme to form a precipitate on a surface of the metal structure.

BRIEF DESCRIPTION OF DRAWINGS

The above and other aspects, features, and advantages of the present disclosure will be more clearly understood from the following detailed description, taken in conjunction with the accompanying drawings, in which.

DETAILED DESCRIPTION

Figure 1:
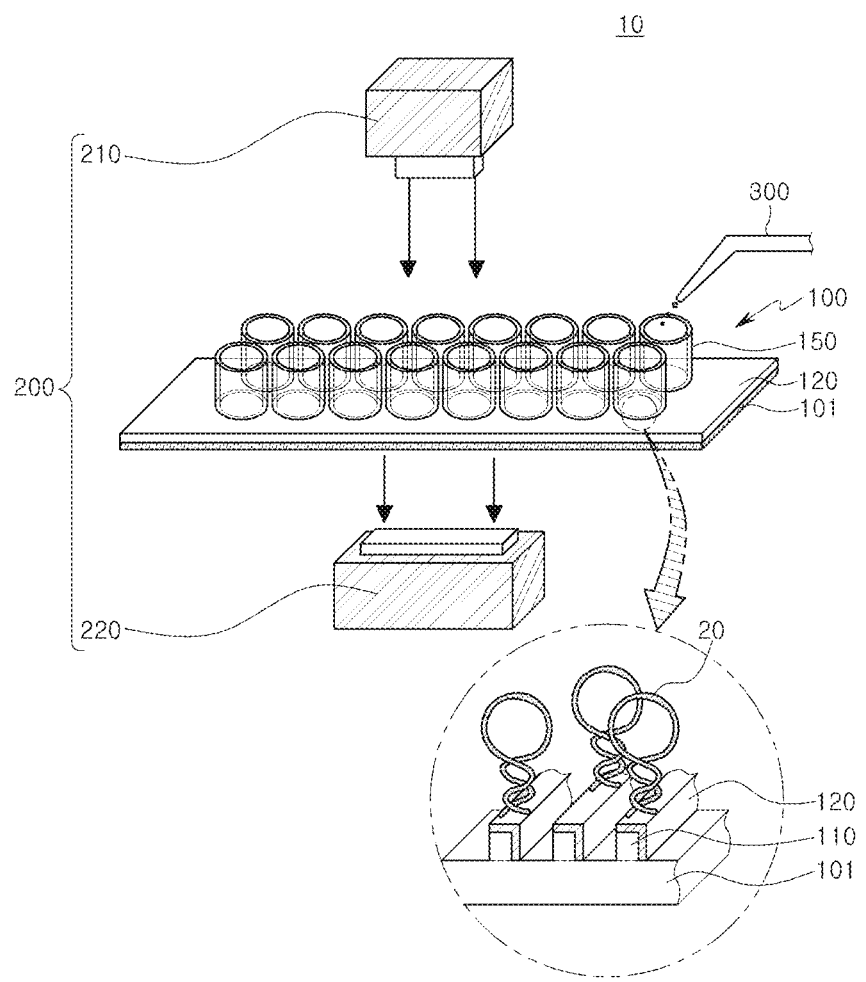
FIG. 1 is a schematic cross-sectional view of a nanoplasmonic sensor according to an exemplary embodiment.

Hereinafter, embodiments of the present disclosure will be described as follows with reference to the attached drawings.

Embodiments of the present disclosure may be modified into various other forms, or various embodiments may be combined, and the scope of the present disclosure is not limited to embodiments to be described below. Further, embodiments of the present disclosure may be provided to more fully explain the present disclosure to those skilled in the art. Therefore, the shapes and sizes of the elements in the drawings may be exaggerated for clarity, and the elements denoted by the same reference numerals in the drawings are the same elements.

Nanoplasmonic Sensor and Kit for Biomolecular Analysis

FIG. 1 is a schematic cross-sectional view of a nanoplasmonic sensor according to an exemplary embodiment.

Referring to FIG. 1, a nanoplasmonic sensor 10 may include a sensing portion 100 and a measurement portion 200. The sensing portion 100 may sense a change in plasmon resonance characteristics by an analyte, and the measurement portion 200 may detect a change in optical characteristics accordingly. The nanoplasmonic sensor 10 may further include a material supplying portion 300 for supplying an analyte, a material provided for analysis, and the like, to the sensing portion 100.

The nanoplasmonic sensor 10 may be used for detection, measurement, and analysis of biomolecules and chemicals such as a gene, a biotic enzyme, a cell, and a protein, by using a localized surface plasmon resonance phenomenon.

The sensing portion 100 may include a base layer 101, a dielectric grating 110, and a metal structure 120. The sensing portion 100 may further include well-type chambers 150 that distinguish the dielectric grating 110 and the metal structure 120 as predetermined regions. Analysis may be carried out in each of the well-type chambers 150 under conditions identical to or different from each other.

The base layer 101 may be selected from a conventional semiconductor substrate such as a silicon substrate, or an insulating substrate. In particular, the base layer 101 may be a light-transmitting substrate for transmitting a specific light source, and may be made of, for example, polyurethane acrylate (PUA) or polyethylene terephthalate (PET). In an exemplary embodiment, the base layer 101 may be made of a transparent oxide such as titanium oxide ($TiO_2$), tantalum oxide ($Ta_2O_5$), aluminum oxide ($Al_2O_3$), or the like.

The dielectric grating 110 may be disposed on the base layer 101. A plurality of the dielectric gratings 110 may be spaced apart from each other by a predetermined gap in one direction. In addition, the dielectric grating 110 may have a rectangular parallelepiped shape, and may be disposed to extend in one direction. The dielectric grating 110 may be made of a thermosetting material, a thermoplastic material and/or a photocurable material, and may be a polymer resin layer. In accordance with an embodiment, the dielectric grating 110 may be a layer in which an upper portion of the base layer 101 is processed. In this case, the dielectric grating 110 may be formed integrally with the base layer 101. In an exemplary embodiment, the dielectric grating 110 may be made of PUA.

The metal structure 120 may sense an analyte, and may sense an analyte by directly contacting the analyte or by disposing the metal structure 120 close to the analyte. Plasmon resonance characteristic in the metal structure 120 may be changed, and a shape of the electromagnetic field may be changed, by the analyte. The analyte may include, for example, a chemical, or a biomolecule such as a gene, RNA, DNA, a protein, and the like. The metal structure 120 may be disposed on an upper surface of the base layer 101 to cover an upper surface and one side surface of the dielectric grating 110. The metal structure 120 may have a bent structure on a lower portion of the dielectric grating 110. The metal structure 120 may include at least one of gold (Au), silver (Ag), copper (Cu), aluminum (Al), and platinum (Pt), and may be made of an alloy thereof. A first probe molecule 20 for receiving the analyte may be adsorbed and immobilized on a surface of the metal structure 120. According to embodiments, one or more probe materials may be adsorbed on the surface of the metal structure 120, depending on the analyte, and a type of the probe material may be changed, depending on the analyte.

The measurement portion 200 may include a light source unit 210 disposed on an upper portion of the sensing portion 100 and generating incident light incident on the metal structure 120, and a light receiving unit 220 disposed on a lower portion of the sensing portion 100 and detecting light that may be changed by the analyte placed on a surface or a periphery of the metal structure 120. An SPR sensor, rather than an LSPR sensor, may be generally based on a Kretschmann configuration that irradiates light according to a condition for total reflection to generate a surface plasmon along a surface of a metal thin film, and measures a change in reflected light. In this case, a prism may be attached to a lower portion of the sensing portion 100. Meanwhile, since the nanoplasmonic sensor 10 of the present embodiment uses the LSPR, a light incidence condition for total reflection may be not required. In addition, the light source unit 210 and the light receiving unit 220 may be disposed on upper and lower portions of the sensing portion 100, respectively, to detect light transmitted through the metal structure 120.

The light source unit 210 may generate light having a wavelength of about 200 nm to 2000 nm, and, for example, may generate infrared rays or visible light. In some embodiments, the light source unit 210 may also comprise a polarizer for polarizing incident light. In some embodiments, the light receiving unit 220 may be disposed on the upper portion of the base layer 101, such as the light source unit 210, depending on a material of the base layer 101, and may further include a separate monitoring unit such as a microscope to observe a change of the analyte 30.

The measurement portion 200 may include a UV-Vis spectrometer, which measures a plasmon resonance phenomenon in the metal structure 120, and, for example, scattering, absorption, or extinction characteristics. The measurement portion 200 may measure a change in the analyte such as presence or absence and a chemical reaction of the analyte around the metal structure 120, based on a change in the resonant frequency or a change in scattering, absorption, or extinction value, due to the same.

The material supplying portion 300 may sequentially provide the first probe molecule 20, an analyte, a second probe molecule, an enzyme, and a substrate, to the metal structure 120 in the respective well-type chambers 150. The first probe molecule 20 may be a material for receiving an analyte, and the second probe molecule, the enzyme, and the substrate may be materials for an enzymatic reaction to amplify an LSPR signal. The materials provided by the material supplying portion 300 and the analysis method using the same will be described in more detail with reference to FIGS. 2A to 2E below.

The kit for biomolecule analysis may include a sensing portion 100 including the dielectric grating 110 and the metal structure 120 on the base layer 101. In addition, the kit for biomolecule analysis may further comprise materials provided on the metal structure 120. Specifically, the kit for biomolecule analysis may further include a first probe molecule that is hybridized with an analyte and is bound to a surface of the metal structure 120, a second probe molecule that is hybridized with the first probe molecule at an end not bound to the analyte, an enzyme that is bound to the second probe molecule, and a substrate that reacts with the enzyme to form a precipitate on a surface of the metal structure 120. After completion of the enzymatic reaction in the kit for biomolecule analysis, a plasmon resonance phenomenon in the kit for biomolecule analysis may be measured using an optical characteristic analyzer such as the measurement portion 200 of the nanoplasmonic sensor 10. The above materials and analysis methods using the same will be described in more detail with reference to FIGS. 2A to 2E.

Method for Manufacturing Nanoplasmonic Sensor for Biomolecule Analysis

A sensing portion 100 of a nanoplasmonic sensor 10 may be manufactured by the following process.

First, a dielectric layer may be formed on a base layer 101.

The base layer 101 may be a layer on which a metal structure 120 is subsequently formed on an upper surface thereof, and corresponds to a substrate constituting a portion of the nanoplasmonic sensor. The base layer 101 may be selected from a semiconductor substrate or an insulating substrate. Further, the base layer 101 may be a light-transmitting substrate, and may transmit light having a specific wavelength.

The dielectric layer may be a layer forming a dielectric grating 110 through a subsequent process, may be formed of a thermosetting material, a thermoplastic material, and/or a photocurable material, and may be a polymer resin layer. The dielectric layer may be formed evenly using an air brush, but is not limited thereto. For example, the dielectric layer may be applied on the base layer 101 by a silver spin coating process, a screen printing process, a spray process, or the like. A thickness of the dielectric layer may be determined, depending on a size of the metal structure 120 to be formed.

Next, the dielectric layer may be patterned to form the dielectric grating 110.

The dielectric grating 110 may be formed using a nanoimprint process. In this case, an imprint mold in which a nanosized line pattern is formed may be used. In an exemplary embodiment, the imprint mold may be made of a flexible material, and may be prepared in the form of a roller. In this case, the imprint mold may be made of, for example, polydimethylsiloxane (PDMS). The dielectric layer may be pressed and patterned by the imprint mold to form the dielectric grating 110. When the roller-shaped imprint mold is used as described above, the dielectric grating 110 may be formed with a large area. The method of manufacturing the dielectric grating 110 is not limited thereto, and the dielectric grating 110 may be formed by a photolithography process and an etching process.

Next, a metal material may be deposited on the base layer 101 and the dielectric grating 110 to form the metal structure 120.

The metal structure 120 may be formed on an upper surface of the exposed base layer 101 and on an upper surface and a side surface of the dielectric grating 110. The metal structure 120 may be formed by arranging the base layer 101 and a source of the metal material, such that the base layer 101 and the source of the metal material have a predetermined inclination, and supplying and depositing the source of the metal material to have a predetermined angle with respect to the base layer 101. The metal structure 120 may be formed using a physical vapor deposition (PVD) process such as a thermal evaporation process, an electron beam evaporation process, or a sputtering process.

In this case, depending on an angle, a shape of the formed metal structure 120 may be changed. Accordingly, in the present embodiment, as the metal material is deposited on the upper surface and the one side surface of the dielectric grating 110, the angle may be adjusted, such that the metal structures 120 are not connected between dielectric gratings 110 adjacent to each other. The angle may be, for example, in the range of 20° to 60°, and may be selected at an angle satisfying the following conditions, taking into account a height and a width of the dielectric grating 110, a spacing distance between the dielectric gratings 110, a thickness of the metal structure 120, and the like. In the present embodiment, the metal material may be supplied and deposited at a predetermined angle with respect to the base layer 101, such that a bent portion may be realized only by one deposition process. In addition, the manufacturing process may be simplified because no separate process such as a lift-off process is required.

In this embodiment, since the dielectric grating 110 is not separately removed from the base layer 101, the manufacturing process may be simplified. The present disclosure is not limited thereto. In an exemplary embodiment, the dielectric grating 110 may be removed using a separate wet etching process or the like, such that only the metal structure 120 may be left.

Finally, the nanoplasmonic sensor 10 may be manufactured by respectively arranging a light source unit 210 and a light receiving unit 220 on upper and lower portions of the sensing portion 100 prepared to include the base layer 101, the dielectric grating 110, and the metal structure 120, and by then providing a material supplying portion 300 for providing materials for analysis to the sensing portion 100.

Method for Analyzing Biomolecule Using Nanoplasmonic Sensor

FIGS. 2A to 2E are views illustrating a method for analyzing a biomolecule using a nanoplasmonic sensor according to an exemplary embodiment.

Figure 3A:
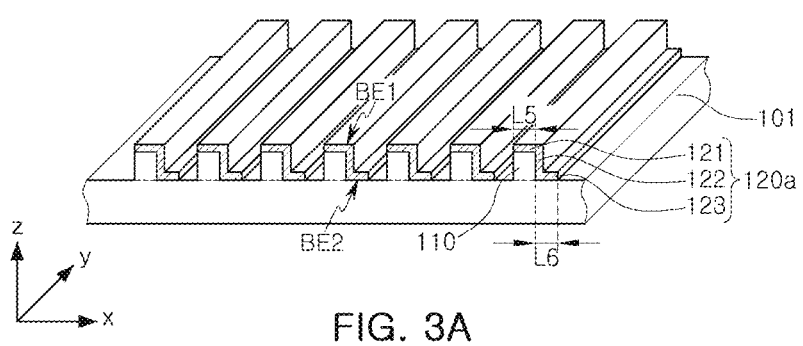
FIGS. 3A and 3B are schematic perspective views illustrating a sensing portion according to an exemplary embodiment.
Figure 3B:
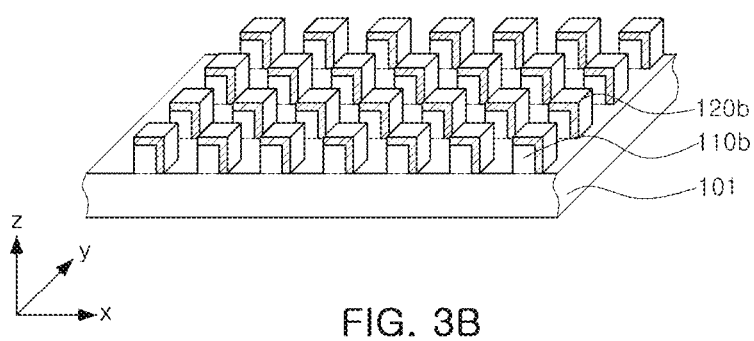

FIGS. 3A and 3B are schematic perspective views illustrating a sensing unit according to an exemplary embodiment.

Figure 2A:
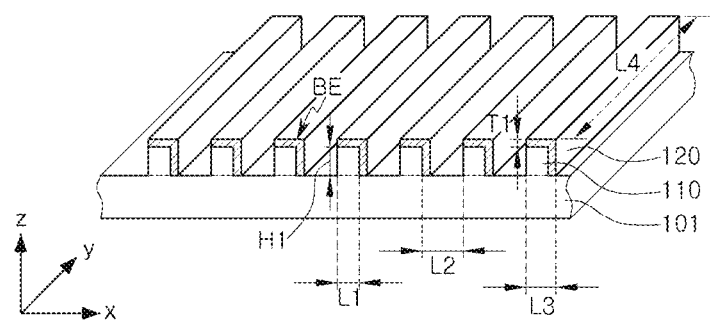
FIGS. 2A to 2E are views illustrating a method for analyzing a biomolecule using a nanoplasmonic sensor according to an exemplary embodiment.

Referring to FIG. 2A, the nanoplasmonic sensor 10 of FIG. 1 or a kit, including a dielectric structure 110, and a metal structure 120 disposed to cover an upper surface and one side of the dielectric grating 110, may be provided.

The dielectric grating 110 may extend in one direction, e.g., in a Y direction, to form a strip. The dielectric grating 110 may have a width having a first distance L1 in an X direction, and may have a first height H1. The first distance L1 may range from 5 nm to 500 nm, and may range, for example, from 50 nm to 90 nm. The first height H1 may range from 20 nm to 500 nm, and may range, for example, from 80 nm to 120 nm. The dielectric gratings 110 may be spaced apart from each other by a gap having a second distance L2 in the X direction. The second distance L2 may range from 40 nm to 500 nm, and may range, for example, from 100 nm to 160 nm. The second distance L2 may be determined to the extent that neighboring metal structures 120 are only formed on one side wall of the dielectric grating 110 and are not connected to each other between neighboring dielectric gratings 110.

The metal structure 120 may have a shape curved along the upper and side surfaces of the dielectric grating 110. For example, the metal structure 120 may have a bent structure including a bent portion BE. Although FIG. 2A illustrates a structure in which the metal structure 120 covers the right side surface of the dielectric grating 110, a shape of the metal structure 120 is not limited thereto. In some embodiments, the metal structure 120 may have a structure covering the left side surface of the dielectric grating 110. The metal structures 120 may be arranged to be spaced apart so as not to contact each other between neighboring dielectric gratings 110. The numbers of the dielectric grating 110 and the metal structure 120 are not limited to those illustrated. In the exemplary embodiment, the sensing portion 100 may include only one dielectric grating 110 and the metal structure 120. The dielectric grating 110 and the metal structure 120 may be separated into predetermined regions by well-type chambers 150 arranged at an upper portion.

A third distance L3, which is the overall width of the metal structure 120, may range from 10 nm to 500 nm, and may range, for example, from 70 nm to 130 nm. The metal structure 120 may be disposed to extend along the dielectric grating 110 in an unbent direction. A distance L4 of the metal structure 120 in this direction may be determined in consideration of the size of the sensing portion 100, and may range from several hundreds of nanometers to several tens of centimeters. A thickness T1 of the metal structure 120 may range from 1 nm to 200 nm, and may range, for example, from 10 nm to 50 nm.

A shape of the metal structure 120 is not limited thereto, and may be changed into various shapes as illustrated in FIGS. 3A and 3B.

Referring to FIG. 3A, a metal structure 120a may include a first horizontal portion 121 disposed on an upper surface of a dielectric grating 110, a vertical portion 122 bent from the first horizontal portion 121 and disposed along one side surface or wall of the dielectric grating 110, and a second horizontal portion 123 bent from the vertical portion 122 and disposed along an upper surface of a base layer 101. The first horizontal portion 121 and the second horizontal portion 123 may be bent from the vertical portion 122 but in opposite directions. The metal structure 120a may have a double-bent structure including at least two bent portions BE1 and BE2. The vertical portion 122 may not necessarily be perpendicular to the upper surface of the base layer 101, but may be disposed to be inclined at a predetermined angle with respect to the upper surface of the base layer 101.

A distance L5 of the first horizontal portion 121 on the dielectric grating 110 may be longer than a distance L6 of the second horizontal portion 123 on the base layer 101. Such a structure may be formed to be stably separated from the metal structure 120a. The relative distances of the first horizontal portion 121 and the second horizontal portion 123 are not limited thereto, and may be variously changed in the embodiments. The distance L5 of the first horizontal portion 121 may be in the range of 5 nm to 500 nm, and may be, for example, in the range of 50 nm to 90 nm. The distance L6 of the second horizontal portion 123 may be in the range of 5 nm to 500 nm, and may be, for example, in the range of 20 nm to 60 nm.

Referring to FIG. 3B, a sensing portion 100 may include a base layer 101, a dielectric grating 110b, and a metal structure 120b.

In this embodiment, in a different manner to the embodiment of FIG. 1, the dielectric grating 110b and the metal structures 120b may have a predetermined distance in a Y direction, and be arranged to be spaced apart from each other. Therefore, the metal structures 120b may have a structure that is spaced apart in both X and Y directions.

Figure 2B:
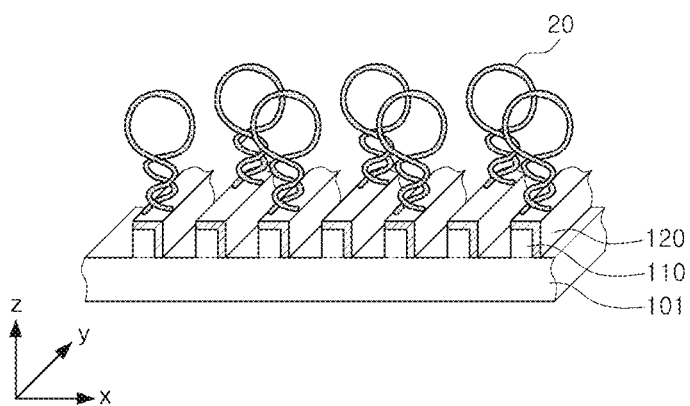

Referring to FIG. 2B, a first probe molecule 20 having a three-dimensional structure may be immobilized, such that one end of the first probe molecule 20 is attached to a surface of a metal structure 120.

The first probe molecule 20 may be a biomolecule including a sequence complementary to an analyte 30 (see FIG. 2C) to be subsequently introduced. The first probe molecule 20 may include, for example, DNA, a peptide nucleic acid (PNA) and a locked nucleic acid (LNA), which is modified form of DNA, and the like. The first probe molecule 20 may be provided in a diluted form in a solution such as a phosphate-buffered saline (PBS).

As illustrated in FIG. 2B, the first probe molecule 20 may be adsorbed on a surface of a metal structure 120 to have a three-dimensional structure having a loop region such as a hairpin structure, in a state in which the analyte 30 is not introduced. For example, the first probe molecules 20 may have a three-dimensional structure, in which one end is adsorbed on the surface of the metal structure 120 and the remaining regions have a loop region, not the double helix structure of general DNA. Therefore, the other end of the first probe molecule 20 may be located close to the metal structure 120. In particular, the loop region may include an end of the first probe molecules 20 furthest away from the metal structure 120. The first probe molecule 20 may have a structure such as a G-quadruplex, in addition to the hairpin structure as illustrated. The first probe molecule 20 may be immobilized to have a hairpin structure on the surface of the metal structure 120, for example, to have a stable hairpin structure on the surface of the metal structure 120 by performing an annealing operation at a temperature range of 90° C. or higher to remove non-covalent bonds present in the solution, and, then, performing a cooling operation in a temperature range of 10° C. or lower. After the first probe molecule 20 is immobilized, the remaining first probe molecules 20 and the like may be cleaned with PBS.

The first probe molecule 20 may be prepared to have a specific functional group in advance to be easily immobilized on the metal structure 120. As a result, the first probe molecule 20 may be stably bound to the surface of the metal structure 120 made of gold (Au), and may form a self-assembled monolayer according to an embodiment. As such, the first probe molecule 20 may be processed to have a specific functional group, depending on a material of the metal structure 120.

In one embodiment, when the analyte 30 is microRNA (miRNA), the first probe molecule 20 may be LNA. LNA may have a structure similar to DNA, but may be bound strongly to complementary oligonucleotides, and therefore may exhibit a relatively high sequence specificity without additional labeling operation.

Figure 2C:
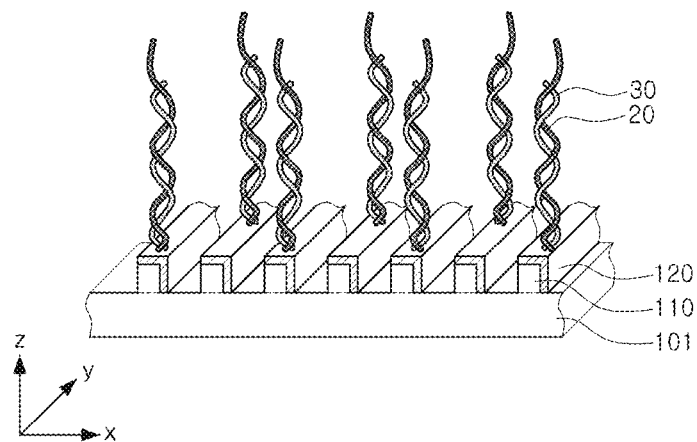

Referring to FIG. 2C, an analyte 30 may be introduced to the metal structure 120 on which the first probe molecule 20 is immobilized, and may be hybridized with the first probe molecule 20.

The analyte 30 may be a biomolecule to be detected, for example, miRNA, DNA, RNA, a small molecule, an antigen, a protein, and the like. In particular, the analyte 30 may include a gene, but is not limited thereto. The analyte 30 may have a base sequence complementary to the first probe molecule 20, and may be complementarily matched with and bound to the first probe molecule 20 by a hybridization operation. The analyte 30 may be dissolved and provided in a buffer solution such as PBS.

The first probe molecule 20 may be bound to the analyte 30, in a melting state in which the three-dimensional structure is released, while one end thereof is spaced away from the metal structure 120. For example, a binding between the first probe molecule 20 and the analyte 30 may be stronger than a binding that forms the three-dimensional structure in the first probe molecule 20, and sequence specificity may be secured by such a binding. As illustrated in FIG. 2C, the analyte 30 may have a shorter length than the first probe molecule 20, and may be bound to a lower end of the melted first probe molecule 20. Therefore, since the entire analyte 30 is bound to the first probe molecule 20, sequence specificity may be further secured. Hybridization may be performed at a melting temperature of about 60° C. or higher for the purpose of melting the first probe molecule 20. The melting temperature, and a concentration of the salt in the solution containing the analyte 30 may be selected such that only the analyte 30 may be bound to the first probe molecule 20, and may be changed, depending on materials of the analyte 30 and the first probe molecule 20. Thereafter, the metal structure 120 may be cleaned with a solution such as PBS to remove remaining unbound materials, and may be cooled to a temperature within a range of about 10° C. or lower to form a hairpin structure again by the first probe molecule 20 not bound to the analyte 30. Therefore, a first probe molecule 20 not bound to the analyte 30 may remain in a state that the first probe molecule 20 is not bound to a second probe molecule 40 in a subsequent operation.

Figure 2D:
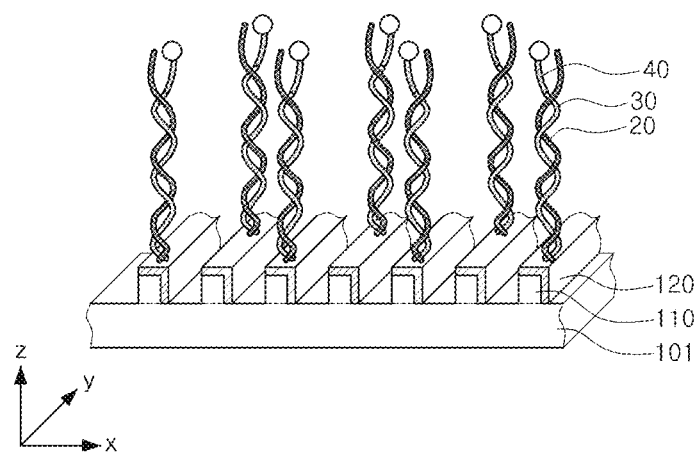

Referring to FIG. 2D, the second probe molecule 40 may be bound to the analyte 30, to provide a second probe molecule 40 that is hybridized with the first probe molecule 20.

The second probe molecule 40 may be bound to an end of the analyte 30, and may have a sequence complementary to a sequence not bound to the analyte 30 in the first probe molecule 20, to be hybridized with a portion of the first probe molecule 20. The second probe molecule 40 may include, for example, DNA, PNA, LNA, and the like, and, in particular, may include functional groups, atomic groups, and/or molecular end groups. Thereby, the second probe molecule 40 may be bound to an enzyme 50 subsequently.

Figure 2E:
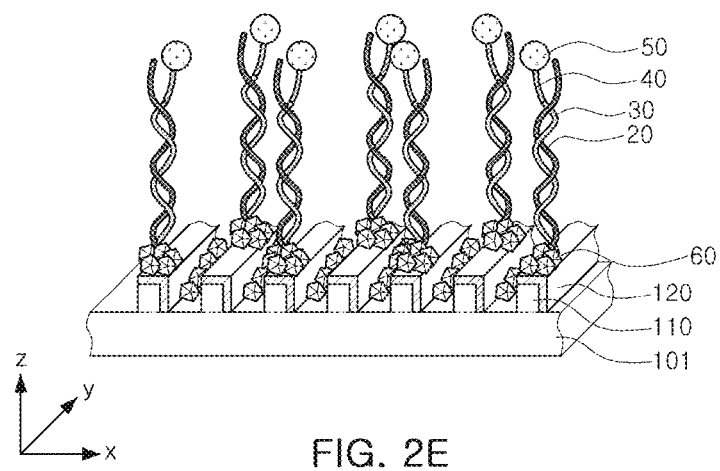

Referring to FIG. 2E, an enzyme 50 and a substrate may be provided to bind the enzyme 50 to the second probe molecule 40, and to induce an enzymatic reaction with the substrate to form a precipitate.

The enzyme 50 may be a protein material for an enzymatic reaction, and may be a material capable of forming a binding with the second probe molecule 40. The enzyme 50 may be, for example, horseradish peroxidase (HRP), alkaline phosphatase (AP), or beta-galactosidase. In particular, the enzyme 50 may be a functional group, an atomic group, and/or a molecular end group capable of performing a biotin-streptavidin binding, a digoxigenin(DIG)-antiDIG binding, or a host-guest interaction, with the second probe molecule 40.

The substrate may be a material that reacts with the enzyme 50 to form a precipitate. The substrate may be, for example, at least one of 4-chloronaphthol (4-CN), 3,3'-diaminobenzidine (DAB), 3-amino-9-ethylcarbazole (AEC), 3,3',5,5'-tetramethylbenzidine (TMB), 5-bromo-4-chloro-3-indolyl phosphate (BCIP)/nitro blue tetrazolium (NBT), 4-chloro-2-methylbenzenediazonium (TR)/3-hydroxy-2-naphthoic acid 2,4-dimethylanilide phosphate (Naphthol AS-MX phosphate), 5-bromo-4-chloro-3-indolyl β-D-galactopyranoside (X-gal), 3,4-cyclohexenoesculetin β-D-galactopyranoside (SGAL), 5-bromo-3-indolyl β-D-galactopyranoside (Bluo-gal), and 6-chloro-3-indolyl-β-D-galactopyranoside (RED-GAL). When 4-CN is used, an enzymatic reaction may be carried out relatively easily. When BCIP/NBT is used, an amount of the precipitate may be relatively increased.

The enzyme 50 may convert a water-soluble substrate to a water-insoluble product by an enzymatic reaction. A precipitate 60 formed by an enzymatic reaction may be adsorbed onto a surface of the metal structure 120. A thickness of the precipitate 60 may be determined, depending on a concentration of the analyte 30, a concentration of the enzyme 50, a type of the enzyme 50, a time of the enzymatic reaction, a type of the substrate, and the like. After the precipitate 60 is formed, a localized surface plasmon resonance phenomenon such as a change in absorbance at the sensor 10 may be measured. The precipitate 60 may be formed on a surface of the metal structure 120 to change a refractive index around the metal structure 120. Therefore, a sensitivity of the sensor 10 may be enhanced by amplifying an LSPR signal.

Figure 4:
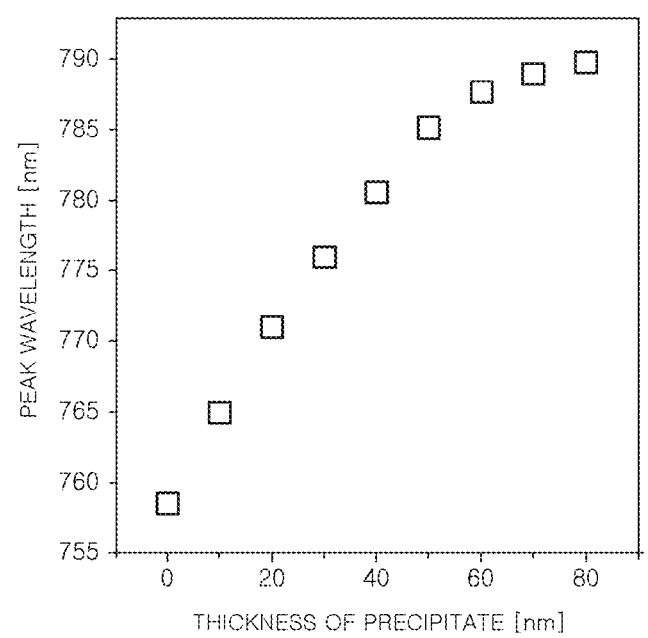
FIG. 4 is a graph simulating analysis results according to a thickness of a precipitate in an analysis method using an exemplary nanoplasmonic sensor.

FIG. 4 is a graph simulating analysis results according to a thickness of a precipitate in an analysis method using an exemplary nanoplasmonic sensor.

Referring to FIG. 4, the results of simulations performed on a structure in which, in the sensing portion 100 of FIG. 1, the dielectric gratings 110 are arranged at a period of 200 nm with a width of 70 nm and a height of 90 nm, and the metal structure 120 has a thickness of 30 nm, are illustrated. Further, in this case, the base layer 101 and the dielectric grating 110 may have a refractive index of 1.5, the precipitate 60 of FIG. 2E may have a refractive index of 1.6, and the sensing portion 100 may be present in a medium having a refractive index of 1.33.

As illustrated in FIG. 4, as a thickness of the precipitate 60 increases within the range of 80 nm, a peak wavelength at the measured absorbance may increase. This indicates that as a thickness of the precipitate 60 increases, shift of absorbance spectrum may increase. Since sensitivity of the sensor 10 increases as the precipitate 60 is formed thicker, a concentration and a type of the enzyme 50, a time of the enzymatic reaction, a type of the substrate, and the like may necessarily be selected appropriately, such that the precipitate 60 is formed to have a certain thickness or more. For example, in embodiments, the thickness of the precipitate 60 may be controlled to be 10 nm or more, for example, 30 nm or more. It can be seen that, when the thickness of the precipitate 60 becomes thicker than a predetermined thickness, for example, 80 nm or more, as the distance of the precipitate 60 from the upper region and the metal structure 120 becomes longer, the shift of the spectrum may be saturated, not improved any longer.

Example of Method for Analyzing Biomolecule

Hereinafter, one embodiment of the present disclosure will be described in detail with reference to FIGS. 1 to 2E together. However, the following examples are illustrative of the present disclosure, but the present disclosure is not limited to the following examples.

A nanoplasmonic sensor 10 was formed to include dielectric gratings 110 on a base layer 101 made of PUA. The dielectric gratings 110 were formed by performing an imprint process using a PDMS mold and a roll-to-roll method, and were formed to have a width of 100 nm at a period of 200 nm. Metal structures 120 were formed by depositing gold (Au) at an angle of 35° using a thermal evaporation process. The dielectric gratings 110 were arranged at a period of 200 nm with a width of 70 nm and a height of 90 nm, and the metal structure 120 was formed with a thickness of 30 nm.

LNA, which is a first probe molecule 20, may be prepared by performing a treatment operation for having a thiol group, a dilution operation using phosphate-buffered saline (PBS) at a concentration of 10 μM, an annealing operation at a temperature range of about 95° C. for about 5 minutes, and a cooling operation slowly. By such operations, relatively weak bonds between bases in the solution may be removed. Therefore, the first probe molecule 20 having a stable hairpin structure may be prepared. A PBS solution in which the LNA is dissolved may be supplied onto the metal structure 120 together with 3-mercapto-1-propanol to control a concentration of LNA, and the metal structure 120 may be cleaned with PBS. The LNA, which is the first probe molecule 20, may be self-assembled on the metal structure 120 to form a self-assembled monolayer.

miRNA, an analyte 30, may be provided in a predetermined concentration of total RNA dissolved in a buffer solution or PBS, and may be bound to the first probe molecule 20 at room temperature. After a hybridization operation proceeded at a melting temperature of about 70° C. for about 1 hour, the metal structures 120, and the like, may be cleaned with PBS, and the sensor 10 in PBS after the washing operation may be cooled to about 4° C. Therefore, the LNA, which is the first probe molecule 20 not bound to the analyte 30, may have a hairpin structure, and, in this case, may not be bound to a second probe molecule 40 in a subsequent operation.

Biotinylated DNA as a second probe molecule 40 may be provided by being dissolved in PBS at a concentration of about 500 nM. After a hybridization operation proceeded for about 3 hours, the sensor 10 may be cleansed with PBS, and may be incubated for about 1 hour in PBS containing about 1% bovine serum albumin (BSA). By blocking with BSA, an enzyme 50 may be prevented from non-specifically adsorbing to a surface of the metal structure 120 in a subsequent operation.

The enzyme 50 may be provided to the sensor 10 in a concentration of about 25 μg/mL of the streptavidin-HRP binding solution in PBS containing 1% BSA for 1 hour. After washing with PBS, the sensor 10 may be incubated in a mixture of 980 μL of 4-CN solution and 20 μL of 100 mM hydrogen peroxide ($H_2O_2$) for about 10 minutes. The hydrogen peroxide may play a role in inducing an enzymatic reaction of HRP.

Figure 5A:
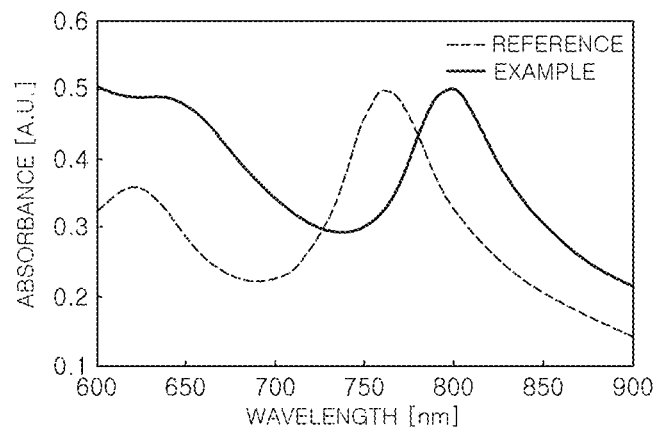
FIGS. 5A and 5B are graphs illustrating measurement results using an exemplary nanoplasmonic sensor.
Figure 5B:
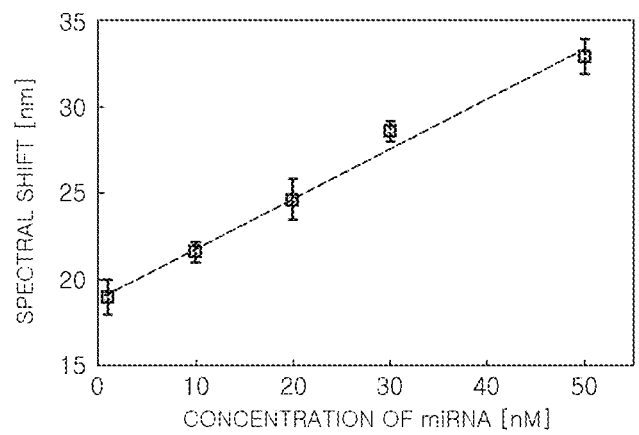

FIGS. 5A and 5B are graphs illustrating measurement results using an exemplary nanoplasmonic sensor.

Referring to FIGS. 5A and 5B, as the measurement results of absorbance using the nanoplasmonic sensor according to the embodiment, an Example in which an analyte 30 is not present ("REFERENCE"), and an Example in which an analyte 30 is miR-let-7a, which is one of miRNA, are illustrated. In the cases of the Examples, the results in which the absorption spectrum is shifted are illustrated, as illustrated in FIG. 5A. As a concentration of the analyte 30 increases, a degree of spectral shift may increase, as illustrated in FIG. 5B. When a concentration of the analyte 30 was 100 nM, a spectral shift of about 37 nm was observed.

Figure 6A:
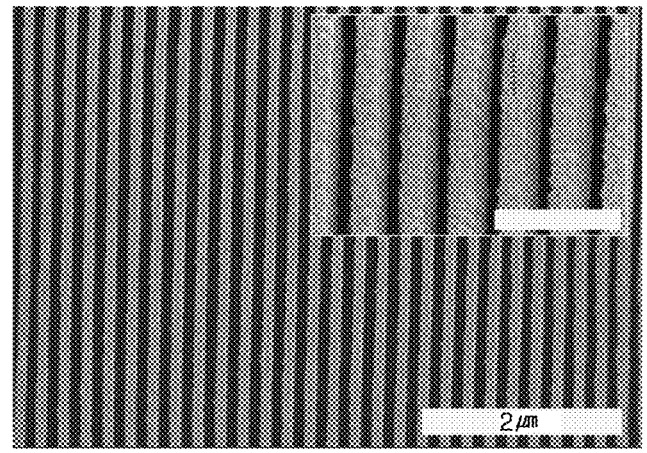
FIGS. 6A and 6B are scanning electron microscopy (SEM) photographs illustrating a sensing portion after analysis using an exemplary nanoplasmonic sensor.
Figure 6B:
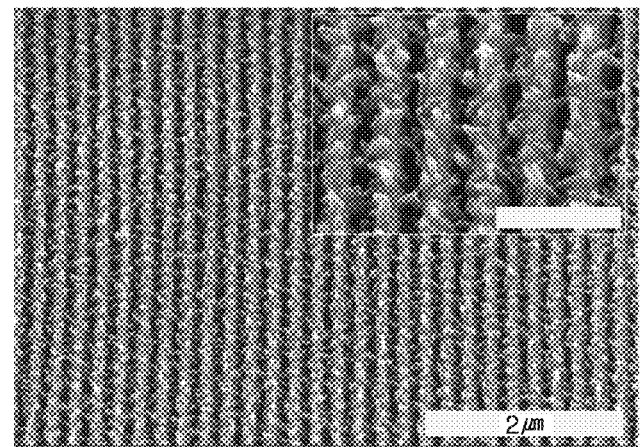

FIGS. 6A and 6B are scanning electron microscopy (SEM) photographs illustrating a sensing unit after analysis using an exemplary nanoplasmonic sensor.

Referring to FIGS. 6A and 6B, a photograph of an Example in which an analyte 30 is not present, and a photograph of an Example in which an analyte 30 is miR-let-7a, are shown. In a case of FIG. 6A, i.e., in a case of an Example in which an analyte 30 is not present, no precipitate 60 by the enzymatic reaction is formed. In a case of FIG. 6B, i.e., in a case of an Example in which an analyte 30 is miR-let-7a, the precipitate 60 by the enzymatic reaction may be adsorbed on the surface of the metal structure 120.

Figure 7A:
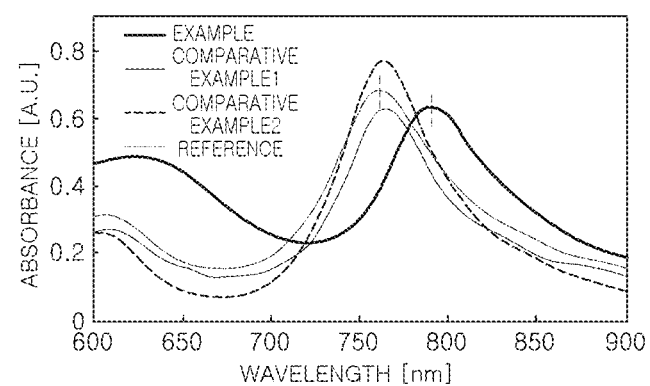
FIGS. 7A and 7B are graphs illustrating measurement results using an exemplary nanoplasmonic sensor.
Figure 7B:
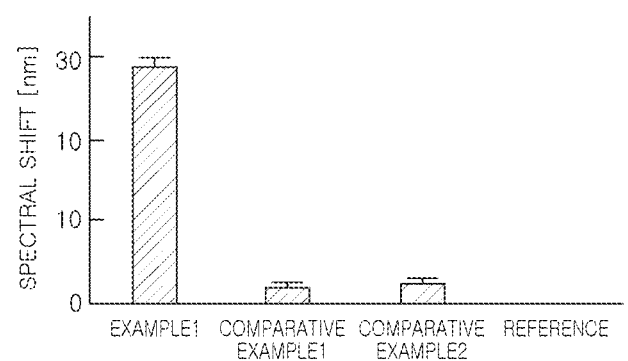

FIGS. 7A and 7B are graphs illustrating measurement results using an exemplary nanoplasmonic sensor.

Referring to FIGS. 7A and 7B, as the measurement results of the absorbance using the nanoplasmonic sensor according to the embodiment, an Example in which an analyte 30 is not present ("REFERENCE"), and an Example, Comparative Example 1, and Comparative Example 2, in which analytes 30 are different miRNAs, respectively, are illustrated. In the cases of the Examples, the results in which miR-let-7a having a base sequence complementary to the first probe molecule 20, which is a let-7a LNA, was measured as the analyte 30, are illustrated. In the cases of the Comparative Examples, the results in which miR-let-7c and miR-let-7f, families of let-7 miRNA, whose base sequences in the first probe molecule 20 are different from each other by one nucleotide, in comparison with the Examples, were measured as the analyte 30, are illustrated.

Table 1 below shows the base sequences of the first probe molecule 20 and the analyte 30. In the base sequence of the let-7a LNA, which is the first probe molecule 20, positions of the LNA were underlined. In the miR-let-7c and miR-let-7f of Comparative Example 1 and Comparative Example 2, portions of the base sequence, which are different from the miR-let-7a of the Example were underlined.

TABLE 1

| Material | Base Sequence |
| --- | --- |
| First Probe Molecule (let-7a LNA) | Thiol-GCCAACTATACAACCTACTACCT CATGTATAGTTGGC |
| Example (miR-let-7a) | UGA GGU AGU AGG UUG UAU AGU U |
| Comparative Example 1 (miR-let-7c) | UGA GGU AGU AGG UUG UAU GGU U |
| Comparative Example 2 (miR-let-7f) | UGA GGU AGU AGA UUG UAU AGU U |

As shown in the graphs of FIGS. 7A and 7B, in the case of the Example, since the base sequences of the first probe molecule 20 and the analyte 30 are complementary, spectral shift may occur. Meanwhile, in the cases of Comparative Example 1 and Comparative Example 2, only one nucleotide was different from those of the Example. When the analysis was performed using the same first probe molecule 20 as those of the Example, substantially no spectral shift was observed. In the cases of Comparative Example 1 and Comparative Example 2, since it may be immobilized to and removed from the first probe molecule 20, it may be removed by washing operation. For this purpose, the melting temperature, and the salt concentration of the solution in which the analyte 30 is provided may be controlled.

According to such results, when analyzing a specific analyte by the analysis method of the present disclosure, only the analyte perfectly matching with the first probe molecule may be detected, and the anylytes having a difference of even one base sequence may be distinguished from each other. Therefore, it can be seen that the specific analyte may be distinguished from materials having similar base sequences, and may be analyzed.

Figure 8A:
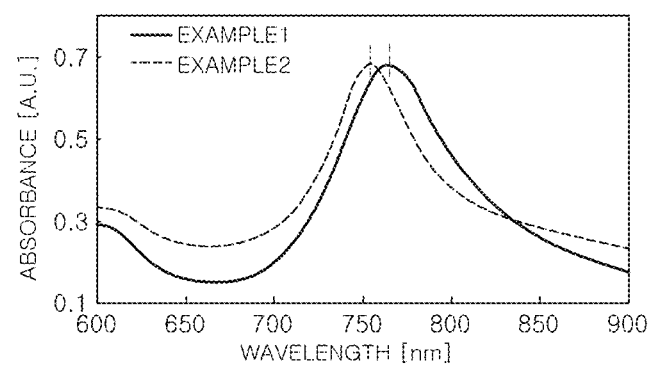
FIGS. 8A and 8B are graphs illustrating measurement results using an exemplary nanoplasmonic sensor.
Figure 8B:
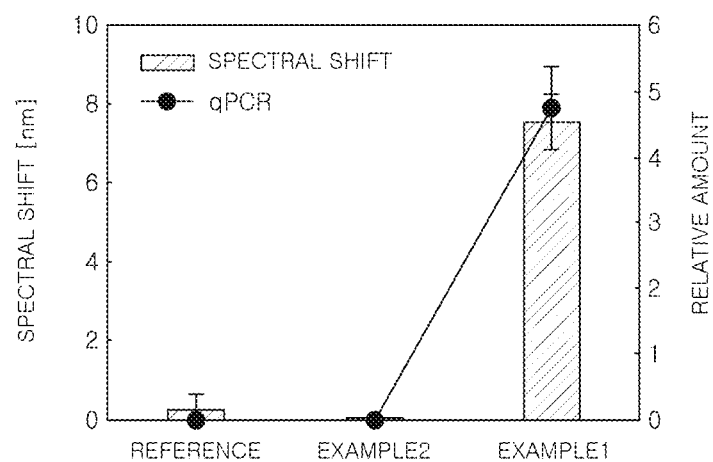

FIGS. 8A and 8B are graphs illustrating measurement results using an exemplary nanoplasmonic sensor.

FIGS. 8A and 8B illustrate the results of detection of miR-200a-2p in total RNA extracted from a stomach adenocarcinoma cell of a human using a nanoplasmonic sensor according to the above Examples. Example 1 is the result for MKN45 cells, and Example 2 is the result for SNU1 cells.

As illustrated in FIG. 8A, shifts of the spectrum and peak in Example 1 were measured. The spectrum of Example 2 was similar to that of a case in which no analyte is provided. FIG. 8B illustrates a bar graph of the degree of spectral shift. These results are consistent with the results of the relative amount analysis of the quantitative polymerase chain reaction (qPCR) illustrated together. Therefore, according to the assay method of the present disclosure, it can be seen that the target material may be accurately sensed even in an environment having many pseudocytes. In the case of PCR analysis, a gene should be amplified to label it separately and analyze it, and it is difficult to perform precise analysis due to deformation of the original state. Meanwhile, it can be seen that the analysis method of the present disclosure may be accurate analysis with a relatively easy method.

The various and advantageous advantages and effects of the present disclosure are not limited to the above description, and may be more easily understood in the course of describing a specific embodiment of the present disclosure.

A nanoplasmonic sensor and kit for molecular analysis may be provided by extending an oscillation path of localized surface plasmon using a metal structure having at least one bent portion, and utilizing a probe molecule that is specifically bound to an analyte, and an enzymatic reaction on a surface of the metal structure In addition, a method of analyzing a biomolecule using the nanoplasmonic sensor and kit for high sensitive biomolecule analysis may be provided.

While exemplary embodiments have been shown and described above, it will be apparent to those skilled in the art that modifications and variations could be made without departing from the scope of the present disclosure as defined by the appended claims.

What is claimed is:

1. A method for analyzing a biomolecule using a nanoplasmonic sensor comprising:
providing the nanoplasmonic sensor including: a plurality of dielectric gratings extending in one direction and spaced apart from each other; wherein each of the plurality of dielectric gratings comprises a metal structure disposed to cover an upper surface and a side surface of a respective dielectric grating of the plurality of dielectric gratings and having at least one bent portion;
immobilizing a first probe molecule on at least one metal structure;
hybridizing an analyte with a first portion of the first probe molecule by introducing the analyte having a base sequence complementary to the first probe molecule, the first portion of the first probe molecule being adjacent to the at least one metal structure;
binding a second probe molecule to an end portion of the analyte such that the second probe molecule is hybridized with a second portion of the first probe molecule that is not bound to the analyte, after the hybridizing the analyte with the first portion of the first probe molecule;
binding an enzyme to the second probe molecule, after the binding the second probe molecule to the end portion of the analyte;
introducing a substrate that reacts with the enzyme to produce a precipitate by an enzymatic reaction; and
measuring localized surface plasmon resonance in the at least one metal structure,
wherein the second probe molecule has a molecular end group that is bound to the enzyme, and
the precipitate is formed on the surface of the at least one metal structure to change a refractive index around the at least one metal structure.

2. The method according to claim 1, wherein the first probe molecule has a hairpin structure in the immobilizing of the first probe molecule.

3. The method according to claim 1, wherein the analyte has a shorter length than a length of the first probe molecule in the hybridizing of the analyte.

4. The method according to claim 1, wherein the analyte is microRNA (miRNA), and the first probe molecule is a locked nucleic acid (LNA).

5. The method according to claim 4, wherein the hybridizing of the analyte includes hybridizing the analyte at a temperature range of 60° C. or higher, and cooling the hybridized analyte to a temperature range of 10° C. or lower.

6. The method according to claim 1, wherein the at least one metal structure includes gold (Au), and the first probe molecule has a thiol group that is bound to the at least one metal structure.

7. The method according to claim 1, wherein the second probe molecule has a biotin molecular end group, and the enzyme has a streptavidin molecular end group.

8. The method according to claim 1, wherein the substrate is at least one of 4-chloronaphthol, 3,3'-diaminobenzidine (DAB), 3-amino-9-ethylcarbazole (AEC), 3,3',5,5'-tetramethylbenzidine (TMB), 5-bromo-4-chloro-3-indolyl phosphate (BCIP)/nitro blue tetrazolium (NBT), 4-chloro-2-methylbenzenediazonium (TR)/3-hydroxy-2-naphthoic acid 2,4-dimethylanilide phosphate (Naphthol AS-MX phosphate), 5-bromo-4-chloro-3-indolyl β-D-galactopyranoside, 3,4-cyclohexenoesculetin β-D-galactopyranoside, 5-bromo-3-indolyl β-D-galactopyranoside, and 6-chloro-3-indolyl-β-D-galactopyranoside.

9. The method according to claim 1,
wherein the nanoplasmonic sensor further comprises a base layer on which the plurality of dielectric gratings are disposed,
wherein the at least one metal structure comprises:
a first horizontal portion disposed on the upper surface of its respective dielectric grating;
a vertical portion bent from the first horizontal portion and disposed along the side surface of the respective dielectric grating; and
a second horizontal portion bent from the vertical portion and disposed along an upper surface of the base layer.

10. The method according to claim 9, wherein the second horizontal portion is bent from the vertical portion in a direction opposite to a bending direction of the first horizontal portion.

11. The method according to claim 1, wherein the at least one metal structure has a total width in a range of 10 nm to 500 nm.

12. The method according to claim 1, wherein the at least one metal structure has a thickness in a range of 1 nm to 200 nm.

* * * * *

SEQUENCE LISTING

```
<160> NUMBER OF SEQ ID NOS: 4

<210> SEQ ID NO 1
<211> LENGTH: 37
<212> TYPE: DNA
<213> ORGANISM: Artificial Sequence
<220> FEATURE:
<223> OTHER INFORMATION: let-7a LNA

<400> SEQUENCE: 1
gccaactata caacctacta cctcatgtat agttggc                              37

<210> SEQ ID NO 2
<211> LENGTH: 22
<212> TYPE: RNA
<213> ORGANISM: Artificial Sequence
<220> FEATURE:
<223> OTHER INFORMATION: miR-let-7a

<400> SEQUENCE: 2
ugagguagua gguuguauag uu                                              22

<210> SEQ ID NO 3
<211> LENGTH: 22
<212> TYPE: RNA
<213> ORGANISM: Artificial Sequence
<220> FEATURE:
<223> OTHER INFORMATION: miR-let-7c

<400> SEQUENCE: 3
ugagguagua gguuguaugg uu                                              22

<210> SEQ ID NO 4
<211> LENGTH: 22
<212> TYPE: RNA
<213> ORGANISM: Artificial Sequence
<220> FEATURE:
<223> OTHER INFORMATION: miR-let-7f

<400> SEQUENCE: 4
ugagguagua gauuguauag uu                                              22
```